United States Patent [19]
Koch et al.

[11] Patent Number: 5,800,335
[45] Date of Patent: Sep. 1, 1998

[54] INCUBATOR FOR TOMOGRAPHIC EXAMINATIONS

[75] Inventors: Jochim Koch, Ratzeburg; Wolfgang Franz, Lübeck, both of Germany

[73] Assignee: Drägerwerk Aktiengesellschaft, Lübeck, Germany

[21] Appl. No.: 841,382

[22] Filed: Apr. 30, 1997

[30] Foreign Application Priority Data

May 3, 1996 [DE] Germany ................ 196 17 739.1

[51] Int. Cl.$^6$ .................................................. A61G 11/00
[52] U.S. Cl. ................................................................. 600/22
[58] Field of Search ................... 600/21-22; 128/897-98

[56] References Cited

FOREIGN PATENT DOCUMENTS 243986  3/1989  Japan ......................... 600/22

Primary Examiner—John P. Lacyk
Attorney, Agent, or Firm—Walter Ottesen

[57] ABSTRACT

In incubator 1 for tomographic examinations includes a patient section 2 and a supply section 3 which extends from the patient section 2. The patient section includes a cylindrically-shaped double wall section made of transparent plastic. The supply section 3 includes a venturi nozzle 13 which functions to generate a difference pressure and simultaneously supplies air and oxygen. The supply section 3 also includes a heater 14 which is preferably combined with an air humidifier 15 outputting water vapor as well as input and output openings to and from the patient section 2 to ensure a circulating air and oxygen supply in the incubator 1 while at the same time emitting a gas portion to the ambient through openings 20.

11 Claims, 2 Drawing Sheets

5,800,335

INCUBATOR FOR TOMOGRAPHIC EXAMINATIONS

BACKGROUND OF THE INVENTION

Known incubators for newborns and prematures generally have a support surface and a substantially transparent plastic hood which can be opened at least in part. Depending upon the state of the health and age of the patient disposed on the support surface, the air in the incubator is warmed and humidified in order to prevent a cooling and/or dehydration of the patient.

U.S. patent application Ser. No. 08/679,905, filed Jul. 15, 1996, discloses an incubator having an improved conduction of air about the support surface. The circulating air is pumped via a fan unit located below the support surface.

For several years, image producing methods have been applied to improve the diagnosis of illnesses. Various tomographic measuring methods have been utilized and the most well-known thereof include magnetic resonance imaging (also known as magnetic resonance or nuclear spin tomography) and computer tomography operating with x-rays.

Such examinations utilizing image-forming methods are also needed for newborns and prematures. However, the problem here is that the tedious examinations in the appropriate examining apparatus are not possible or are fraught with risk without the protective environment of a suitable incubator. This is so because the patient to be examined is cooled too intensely and is dehydrated. On the other hand, and especially for magnetic resonance tomography, it must be ensured that no magnetic or electromagnetic disturbances falsify or become superposed on the measurements made on the patient in order that the quality of image formation and evaluation is not affected.

SUMMARY OF THE INVENTION

It is an object of the invention to provide an incubator for tomographic examinations wherein microclimatic conditions are maintained which are life-supporting for the patient. However, and simultaneously, no electromagnetic disturbances for the tomographic examinations are generated by the incubator and the incubator, in turn, is not disturbed in its function by the intense magnetic field of the tomograph.

The incubator of the invention includes: a first section for accommodating a patient therein; the first section being defined by a double-wall structure enclosing a space for the patient and being made of transparent plastic to facilitate observation of the patient; means for supplying an air/oxygen mixture for the patient; a second section connected to the first section; apparatus mounted in the second section and the apparatus including a venturi nozzle for passing the air/oxygen mixture into the second section and to establish a difference pressure within the first and second sections to cause the air/oxygen mixture to circulate as a gas flow between the sections; the apparatus further including a heater unit downstream of the venturi nozzle for heating the gas flow passing on to the first section; and, the double-wall structure defining first opening means for conducting a first portion of the gas flow into and from the space for the patient whereat gas such as carbon dioxide enters the gas flow and second opening means for conducting a second portion of the gas flow to the ambient.

A significant advantage of the invention is that no electrically operated or switched components are used which would disturb the actual tomographic examination or would themselves be disturbed with respect to their function. Accordingly, a venturi nozzle arrangement is used which effects the air/gas circulation. With this venturi nozzle arrangement, the electrically driven fan unit, which would otherwise be conventional and necessary, is omitted. A further advantage of the invention is the controlled circulation of air and gas within the incubator in order to, on the one hand, prevent the direct contact of the patient with the air warmed by the heater as long as it is too warm while, on the other hand, to provide a metered ventilation and venting of the patient space.

Finally, the incubator of the invention is in the form of a tube-shaped unit comprising a patient section and a supply section which extends from the patient section in the longitudinal direction. The tube-shaped unit is especially simple to manipulate without hindering or disturbing the tomographic examination of the patient.

BRIEF DESCRIPTION OF THE DRAWINGS

The invention will now be described with reference to the drawings wherein.

DESCRIPTION OF THE PREFERRED EMBODIMENT OF THE INVENTION

Figure 1:
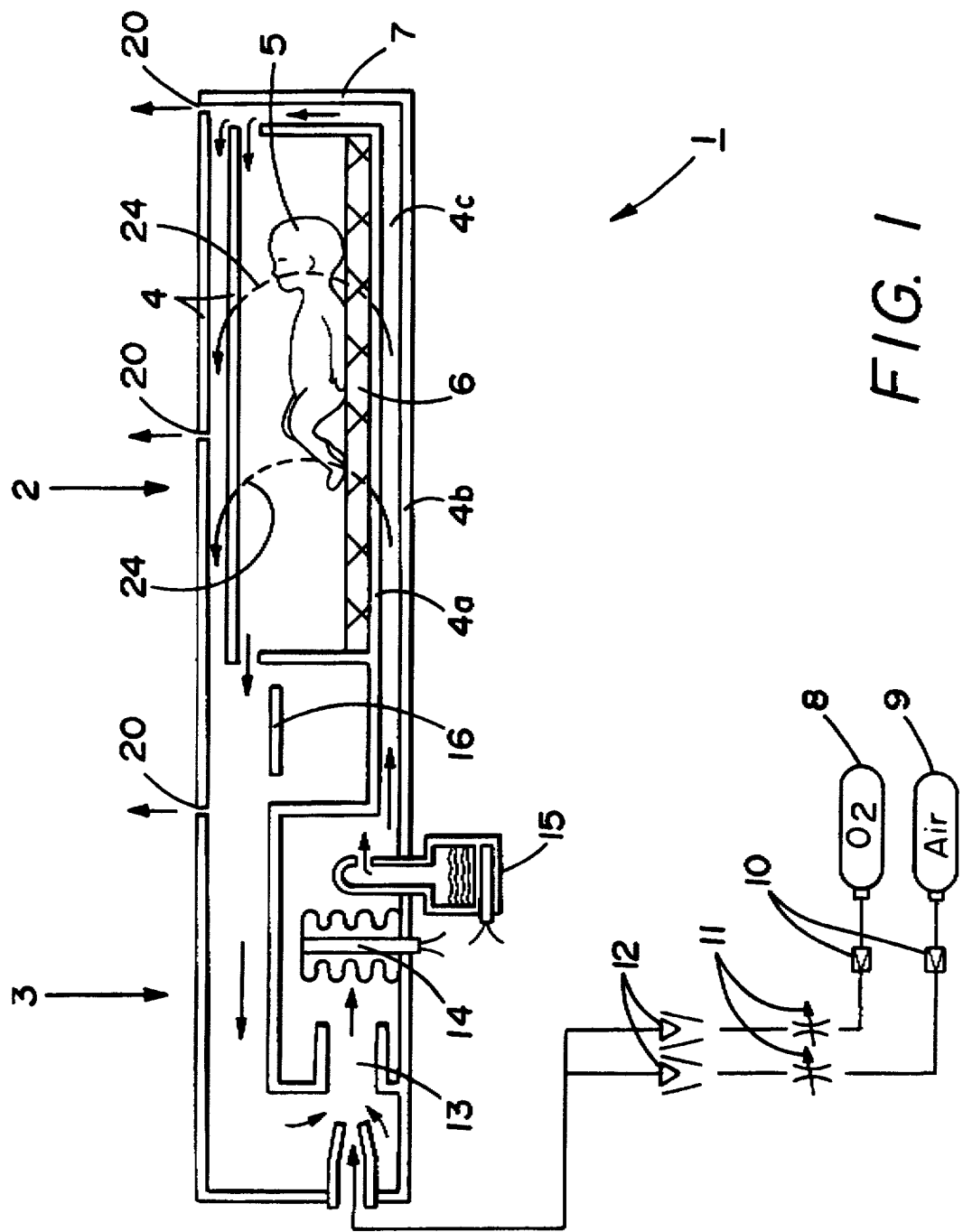
FIG. 1 is a schematic showing the incubator according to the invention including the supply section thereof.

The incubator 1 of the invention includes structure for circulating the air and comprises two sections (2, 3) which are arranged one behind the other in the longitudinal direction and are connected so that gas can flow therebetween. The incubator can be inserted into a corresponding measuring coil of a tomograph with the end face 7 being inserted first. The patient section 2 is configured so as to have a tubular shape and is defined by a peripherally extending double wall 4 including an inner wall 4a and an outer wall 4b. The double wall 4 is preferably made of a polymethacrylate such as polymethyl methacrylate (PMMA) in order to be able to visually monitor the patient 5 externally because of the excellent transparency of this material.

The upper region of the patient section 2 is provided with a removable cover (not shown) or a suitable hood which can be opened via hinges to facilitate removal of the patient 5 from the patient section 2 or to place the patient on the mattress 6. A channel-shaped air/oxygen inflow from the supply section 3 is provided in the lower region of the double wall 4. The gas mixture rises in the annular space 4c of the double wall about the patient 5 because of the pressure difference generated in the supply section 3. A portion of the gas flow rises in the double-walled region of the end portion 7 of the incubator 1 so that the circulating air is simultaneously guided axially to the end portion 7 and circularly upwardly within the annular space 4c. The lower region of the double wall 4 also serves as the support surface for receiving a patient 5 lying on the heat-insulating mattress 6. The broken lines 24 indicate the concentric gas flow direction in the annular space 4c of the double wall 4 with the gas flow flowing in the peripheral direction. The short arrows indicate the gas flow in the end portion 7 of the double wall 4 into the interior space of the patient section 2 as well as again out of this inner space. The small arrows also show the gas flow through openings 20 out of the incubator 1 to the ambient air.

The supply section 3 of the incubator 1 is built up as described below to heat and ventilate the patient section 3 utilizing the air circulation principle wherein a portion of the gas flow is continuously renewed.

Oxygen and air are supplied, for example, by pressure cylinders (8, 9). A venturi nozzle 13 or a corresponding arrangement of several venturi nozzles arranged especially in parallel are driven with the aid of this oxygen and air via pressure reducers 10, metering valves 11 and volume flow sensors 12. The venturi nozzle 13 is driven so that a difference pressure is generated which effects a circulation of the air/oxygen mixture in the incubator 1 and supplies the needed thermal exchange.

Figure 2:
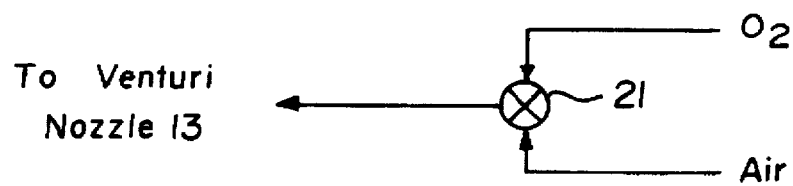
FIG. 2 is a schematic showing an alternate embodiment for supplying an air/oxygen mixture to the venturi nozzle of the incubator; and, FIG. 3 is a schematic showing the circuit for switching the heater of the incubator on and off.

Oxygen and air can be taken from a central supply unit in lieu of utilizing elements 8, 9 and 10. Also, a mixer 21 can be used in lieu of elements 11 and 12 as shown in FIG. 2. The mixer 21 is used in a hospital environment where the gases are supplied from a central gas supply.

The controlled mixing of air and oxygen of the drive gas of the venturi nozzle 13 permits an adjustment of any desired oxygen concentration in the patient section 2 and therefore in the respiratory air of the patient 5 because the drive gas passes along the flow path (indicated by the arrows) to the patient section 2 in the selected composition.

Components, which emit electromagnetic radiation (such as microprocessors), are avoided for controlling the operation of the supply section 3. Electrical components such as transformers or motors are also omitted which are disturbed with respect to their function by the magnetic field of the tomograph. The control of the temperature via the heater 14 takes place with the aid of a switched two-point controller (not shown) having sensor 16 for measuring temperature. The heater 14 is connected to the output of the two-point controller.

Figure 3:
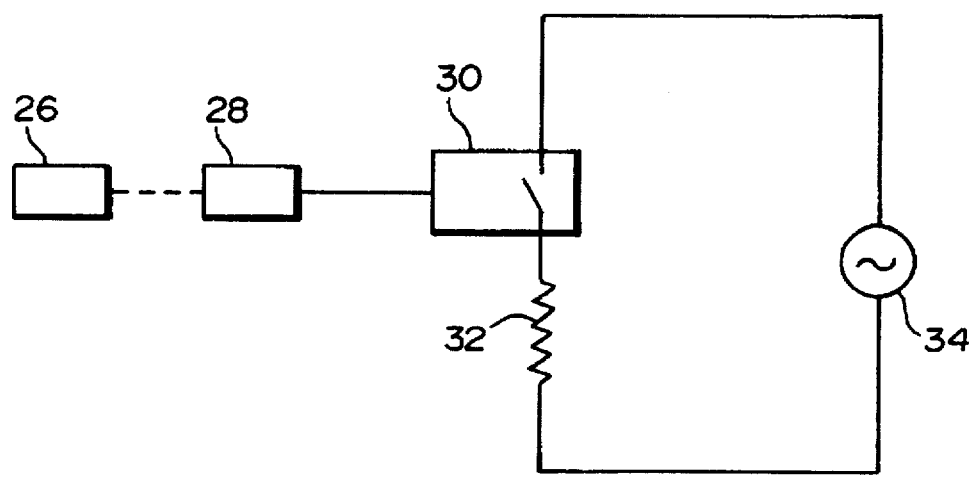

In the embodiment shown in FIG. 3, a liquid expansion system 26 functions as a sensor and operates on a microswitch 28. The liquid expansion system 26 is a temperature sensor mounted in the incubator 1 and is based on the effect of the expansion of a liquid when the temperature increases. The microswitch 28 is switched off when the desired temperature is reached in the incubator 1. The microswitch 28 does not directly switch the heater 14 on and off because of the switching spark which would occur. Rather, the microswitch drives a semiconductor or solid state relay 30 with minimal switching power. The semiconductor relay 30, in turn, switches the heater element 32 of heater 14 on and off at the zero crossover of the alternating voltage 34 without generating disturbing electromagnetic radiation.

In the embodiment shown in FIG. 1, a water heater 15 functions as an air humidifier and is located behind the heater 14 as viewed in flow direction. The air humidifier is provided for the circulating air/gas mixture. This is especially important for prematures in order to avoid heat loss because of water evaporation. These losses are greatly reduced with a high ambient air humidity.

The supplied air/oxygen mixture generates a difference pressure in accordance with the venturi principle and this difference pressure causes a circulation of the air in the incubator 1 and thereby ensures the needed thermal exchange. Carbon dioxide is expelled from the interior patient space between mattress 6 and the peripherally extending double wall 4 because of the continuous supply of fresh gas and the gas losses of the incubator 1 via the openings 20 provided in the upper region of the outer wall. The openings 20 are in the form of gaps and the exiting gas is indicated by the short upward outflow arrows.

The supply section 3 includes the air circulating device having venturi nozzle 13, heater 14 and air humidifier 15 and the corresponding control and is mounted remote from the patient section 2 with the patient 5. The corresponding control can be the general embodiment of the two-point controller or the more specific embodiment shown in FIG. 3. In this way, the supply section 3 is less influenced by magnetic forces of the examining coil and the supply section 3 influences and disturbs less the sensitive measurement signals of the measuring coil. The air guidance in the patient section 2 takes place in the annular space 4c of the double wall 4. Heat losses occur only at the outer wall 4b. The inner wall 4a is therefore held to a warmer temperature than the outer wall 4b and the radiation losses of the patient 5 are reduced. The patient 5 furthermore does not come into direct contact with the air heated in the supply section 3 by the heater 14. In this way, the danger of burns is precluded.

A portion of the circulating air is conducted directly over the inner space of the patient section 2 in order to contribute to a heat exchange and an air exchange, especially for expelling carbon dioxide. In the embodiment shown, a constant volume flow of oxygen and air of approximately 30 liters per minute is adjusted. The incubator 1 is, in the example, so dimensioned that for a controlled gas emission to the ambient via the openings 20 of approximately 30 liters per minute, a circulated volume flow of approximately 100 liters per minute remains (flowing back to venturi nozzle 13).

It is understood that the foregoing description is that of the preferred embodiments of the invention and that various changes and modifications may be made thereto without departing from the spirit and scope of the invention as defined in the appended claims.

What is claimed is:

1. An incubator comprising:
   a first section for accommodating a patient therein;
   said first section being defined by a double-wall structure enclosing a space for the patient and being made of transparent plastic to facilitate observation of the patient;
   means for supplying an air/oxygen mixture for the patient;
   a second section connected to said first section;
   apparatus mounted in said second section and said apparatus including a venturi nozzle for passing said air/oxygen mixture into said second section and to establish a difference pressure within said first and second sections to cause said air/oxygen mixture to circulate as a gas flow between said sections;
   said apparatus further including a heater unit downstream of said venturi nozzle for heating the gas flow passing on to said first section; and,
   said double-wall structure defining first opening means for conducting a first portion of said gas flow into and from said space for the patient whereat gas such as carbon dioxide enters the gas flow and second opening means for conducting a second portion of the gas flow to the ambient.

2. The incubator of claim 1, said apparatus further including a humidifier for emitting water vapor to said gas flow and said humidifier being mounted in said second section downstream of said heater unit.

3. The incubator of claim 2, wherein said double-wall structure has a substantially cylindrical configuration.

4. The incubator of claim 2, wherein said first and second sections are arranged one behind the other to conjointly define an elongated structure.

5. The incubator of claim 2, said supply means comprising pressure vessels for supplying the air and oxygen of said air/oxygen mixture.

6. The incubator of claim 2, said supply means comprising a central source for the air and oxygen of said air/oxygen mixture and a gas mixer for mixing the air and oxygen to form said air/oxygen mixture.

7. The incubator of claim 2, wherein said supply means supplies said air/oxygen mixture to said incubator at a rate of 10 to 40 liters per minute and said second portion including said gas flow flows to the ambient also at a rate of 10 to 40 liters per minute.

8. The incubator of claim 2, wherein the gas flow circulated in said incubator less the gas flow expelled via said second opening means is in the range of approximately 80 to 160 liters per minute.

9. The incubator of claim 2, wherein said plastic of said double-wall structure of said first section is polymethacrylate.

10. The incubator of claim 9, wherein said polymethacrylate is polymethylmethacrylate (PMMA).

11. The incubator of claim 1, said heater unit including:

a heater;

an alternating voltage supply;

a microswitch;

a temperature-dependent sensor device mounted in said incubator and adapted to operate on said microswitch;

a semiconductor relay connected to said microswitch to be controlled thereby to switch said heater on and off by connecting and disconnecting said alternating voltage supply to said heater; and, said semiconductor switch being adapted to switch said heater on and off when the alternating voltage of said alternating voltage supply passes through zero.

* * * * *